United States Patent [19]

Demarcq

[11] 4,059,656
[45] Nov. 22, 1977

[54] PROCESSES FOR NEUTRALIZING 2,3-DIBROMOPROPANOL PHOSPHORIC ACID ESTERS CONTAINED IN TRIS(2,3-DIBROMO-1-PROPYL) PHOSPHATE

[75] Inventor: Michel Demarcq, Lyon, France

[73] Assignee: Produits Chimiques Ugine Kuhlmann, Paris, France

[21] Appl. No.: 672,988

[22] Filed: Apr. 2, 1976

[30] Foreign Application Priority Data

Apr. 25, 1975  France ................................. 75.2982

[51] Int. Cl.$^2$ ................................................. C07F 9/09
[52] U.S. Cl. ..................................... 260/990; 260/963
[58] Field of Search ...................... 260/990, 978, 963

[56] References Cited

U.S. PATENT DOCUMENTS 2,928,859  3/1960  Preston et al. ................... 260/978 X

FOREIGN PATENT DOCUMENTS 1,198,196  12/1959  France ................................. 260/990

OTHER PUBLICATIONS

Fitch, "J. Am. Chem. Soc.", vol. 86, [1964], pp. 61–64.

*Primary Examiner*—Anton H. Sutto
*Attorney, Agent, or Firm*—Brooks, Haidt, Haffner & Delahunty

[57] ABSTRACT

Processes for the neutralization of tris(2,3-dibromo-1-propyl) phosphate containing certain quantities of phosphoric acidity, and possibly halohydric acidity, which processes comprise heating the phosphate with at least one carbon-containing orthoester, the tris(2,3-dibromo-1-propyl) phosphate so produced being adapted for use as a flame- or fireproofing agent in plastics, synthetic fibers, and paints.

9 Claims, No Drawings

PROCESSES FOR NEUTRALIZING 2,3-DIBROMOPROPANOL PHOSPHORIC ACID ESTERS CONTAINED IN TRIS(2,3-DIBROMO-1-PROPYL) PHOSPHATE

BACKGROUND OF THE INVENTION

The present invention relates to processes for treating tris(2,3-dibromo-1-propyl) phosphates, more simply called dibromopropyl phosphate herein, to render the impurities contained therein harmless for the various intended uses, and more particularly, the present invention relates to processes for neutralizing the crude dibromopropyl phosphate prepared by the reaction of phosphorus oxychloride with dibromopropanol.

Such dibromophosphates contain certain limited quantities of one or both of the following phosphoric acid esters:

$(CH_2Br-CHBr-CH_2O)_2PO(OH)$ $CH_2Br-CHBr-CH_2O-PO(OH)_2$ and possibly also traces of hydrochloric and/or hydrobromic acids, representing altogether a total acidity equivalent to a maximum of about 500 meq/kg. Under ideal conditions the reaction of phosphorus oxychloride with dibromopropanol proceeds according to the equation:

$3\ CH_2Br-CHBr-CH_2OH + POCl_3 \rightarrow$
$(CH_2Br-CHBr-CH_2O)_3PO + 3\ HCl$ (1)

This reaction can be catalyzed by metallic compounds such as magnesium, magnesium chloride, titanium tetrachloride, tetrabutyl titanate $[Ti(OC_4H_9)_4]$, lithium, lithium chloride, and aluminum chloride, as shown in French Pat. No. 1,198,196 (the principal patent and the first addition thereto) and British Pat. No. 1,098,637. Under the usual industrial conditions for carrying out the reaction, the hydrochloric acid by-product causes the cleavage of a certain number of ester linkages and the concomitant formation of phosphoric acid acid esters and of dibromochloropropane by reactions such as:

$(CH_2Br-CHBr-CH_2O)_3PO + HCl \rightarrow$
$(CH_2Br-CHBr-CH_2O)_2PO(OH) +$
$CH_2Br-CHBr-CH_2Cl$ (2)

$(CH_2Br-CHBr-CH_2O)_2PO(OH) + HCl \rightarrow$
$(CH_2Br-CHBr-CH_2O)PO(OH)_2 +$
$CH_2Br-CHBr-CH_2Cl$ (2')

The presence of one or both of the phosphoric esters, $(CH_2Br-CHBr-CH_2O)_2PO(OH)$ and $CH_2BR-CHBr-CH_2O-PO(OH)_2$, in the dibromopropyl phosphate is undesirable for uses such as fireproofing of plastics, synthetic fibers, and paints.

It can generally be attempted to suppress these side reactions by facilitating the removal of the dissolved hydrogen chloride, for example, by conducting the reaction under vacuum or with a flow of inert gas, but it is impossible totally to obviate these side reactions. The answer, as proposed in U.S. Pat. No. 3,046,297, is to operate in the presence of a tertiary amine, but this is uneconomic because of the necessity of adding considerable amounts of diluent as well as the need for multiple and delicate washes to remove the amine chlorohydrate by-product.

In commercial practice, one must accordingly be content in most instances with removing the unwanted phosphoric esters by means of alkaline washes. However, operating in this manner involves the total loss of these acid esters and also creates problems because of the high viscosity of the dibromopropyl phosphates, which in turn leads to difficulties in decantation and mandates again the use of a water-immiscible diluent which must thereafter be separated or removed by distillation. This involves substantial complication of the process, loss of solvent, reduction of production, and it appreciably increases the manufacturing cost.

It was suggested in French Pat. No. 1,198,196 that the acid phosphoric acid esters in the product be converted into neutral dibromopropyl phosphates, instead of being removed. According to this patent, the acid phosphoric esters are converted to neutral esters by reaction with an epoxide according to the reaction:

$(RO)_2P(O)OH + R^1-CH\underset{O}{\overset{\diagdown\ \diagup}{-}}CH-R^2 \rightarrow$
$(RO)_2P(O)-OCHR^1-CHR^2-OH$ (3)

the dibromopropyl radical being represented here, as elsewhere in this disclosure, by R.

A second improvement, described in the first addition to the foregoing Patent, involves converting the terminal hydroxyl group formed in foregoing reaction (3) to an acyloxy group, for instance, by reaction with acetic anhydride:

$(RO)_2P(O)-OCHR^1-CHR^2-OH + Ac_2O \rightarrow$
$(RO)_2P(O)-OCHR^1-CHR^2-OAc + AcOH$ This last procedure does not provide satisfactory results in all instances, particularly when the phosphoric ester is destined to be used in contact with aqueous environments for prolonged times. This is because the mixed dibromopropyl and β-acyloxyalkyl esters formed according to this process are less resistant to hydrolysis than the tris(dibromopropyl phosphate itself.

It is thus necessary to arrange for treatment of the dibromopropyl phosphate obtained by reaction of phosphorus oxychloride with dibromopropanol, leading to a transformation of the impurities to products as stable to hydrolysis as the dibromopropyl phosphate itself.

THE INVENTION

The present invention is based upon the discovery that the phosphoric acid acid esters, as well as the possible traces of hydrohalic materials such as hydrogen chloride or hydrogen bromide present in the crude dibromopropyl phosphate, can be readily and effectively neutralized. Briefly, the present invention provides processes for neutralizing dibromopropyl phosphates, as described herein, which processes comprises reacting at least one carbon-containing orthoester according to the formula:

$Z-C(OY)_3$, (A)

where Z represents a hydrogen atom, a methyl group, a phenyl group, or an OY group, and Y represents an aliphatic radical having up to five carbon atoms or a 2,3-dibromo-1-propyl group.

A wide range of carbon-containing, or carbonic, orthoesters can be used in the practice of the present invention. For example, saturated aliphatic orthoformates such as methyl, ethyl, propyl, isopropyl, n-butyl, n-pentyl, or dibromopropyl and like orthoformates; methyl, ethyl, or dibromopropyl or like orthoacetates; methyl or ethyl or like orthocarbonates; methyl or ethyl or like orthobenzoates; or mixtures of two or more of these give good results. Especially preferred in certain embodiments of this invention are the methyl and ethyl orthoformates and orthoacetates. Not only are these preferred materials commercially available products of relatively low cost, but any excess which is present is readily removed from the neutralized phosphoric acid ester by stripping under vacuum.

The dibromopropyl ortho-esters equally possess desirable characteristics in the practice of the present invention because they permit the conversion of the dibromopropyl mono- and diesters of phosphoric acid present in the tris-dibromopropyl phosphate to the triester of the same alcohol. Thus, they do not introduce a foreign phosphate into the product, although they react less rapidly than the methyl and ethyl materials.

The reaction of the orthoesters of formula (A) with the partial phosphates of the dibromopropyl material occurs according to the following equations:

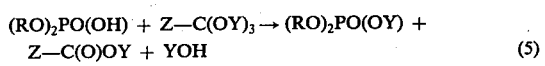

$$(RO)_2PO(OH) + Z-C(OY)_3 \rightarrow (RO)_2PO(OY) + Z-C(O)OY + YOH \quad (5)$$

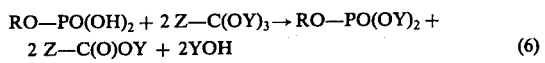

$$RO-PO(OH)_2 + 2\,Z-C(OY)_3 \rightarrow RO-PO(OY)_2 + 2\,Z-C(O)OY + 2YOH \quad (6)$$

The operation of the process according to the present invention comprises adding to the phosphate at least abut a stoichiometic quantity of the orthoester and then heating the mixture for a time sufficient to reduce the acidity to a desired level. In certain embodiments, it is desirable to conduct the heating step under an inert atmosphere, utilizing for example an inert gas such as nitrogen. The process can also be carried out in the presence of an inert solvent, for example, an aliphatic or aromatic hydrocarbon, a chlorinated hydrocarbon, a ketone, or an acetic ester.

The process can then be completed by stripping the reaction mixture under vacuum to free it of all or part of the non-phosphoric components, such as excess orthoester, ZCOOY ester(s), YOH alcohol(s), solvent(s), dibromochloropropane, dibromopropanol, 1,2,3-tribromopropane, and like materials. If desired, the excess orthoester can be recovered and re-used in, or recycled to, the process.

As noted above, the quantity of orthoester is desirably at least about stoichiometric to the acidity and quantities greater than stoichiometric are readily utilized. In general, it is preferred to use as amount of orthoester which is from about one to about five times stoichiometric, and in certain embodiments, it is especially preferred to use from 1.1 to 3 times the stoichiometric quantity of orthoester.

The neutralization is carried out at temperatures of from about 20° to about 200° C, and it is preferred to carry out the neutralization at a temperature of between 70° and 150° C. The time during which the heating is carried out according to this invention desirably ranges from about 15 minutes to about 20 hours. The pressure used can vary, but atmospheric pressure is generally preferred.

The neutralized dibromopropyl phosphate provided by the present process has excellent stability to hydrolysis. It can be used in the same way as pure tris(dibromopropyl) phosphate as a flameproofing agent in materials destined for use in contact with water. Thus, it can be used in polyester and rayon fibers. If desired, it can also be added stabilizers against oxidation or heat or ultraviolet radiation.

The following examples are given to illustrate embodiments of the invention as it is presently preferred to practice it. It will be understood that these examples are illustrative, and the invention is not to be considered as restricted thereto except as indicated in the appended claims.

Unless otherwise indicated, all parts, percentages, proportions, and ratios herein are by weight.

EXAMPLE I

The crude dibromopropyl phosphate utilized in these Examples of neutralization according to the present invention is prepared according to the following type of reaction: A four-liter reactor fitted with an agitator and a reflux condenser is charged with 800 g of dibromopropanol, 180 g of phosphorus oxychloride, and 0.6 g of magnesium. The temperature of the mixture is raised to 90° C, and while this temperature is maintained, 1580 g of dibromopropanol and 360 g of phosphorus oxychloride are simultaneously added dropwise during 45 minutes.

Thereafter, dry nitrogen is bubbled through the mixture to entrain all the hydrochloric acid, and the temperature of the reaction mixture is raised to 100°–115° C. This latter temperature is maintained for 1 hour and 15 minutes, and the reaction mass is then cooled. The crude phosphate obtained weighs about 2350 g.

EXAMPLE II

The crude phosphate prepared according to Example I contains 10.7 meq/kg HCl; 4.2 meq/kg of P—Cl material, and 160 meq/kg of P—OH material. Five hundred grams of this phosphate is heated for one hour at 140° C with 40 g of commercial ethyl orthoformate under a nitrogen atmosphere. The mixture is stripped under a pressure of 1.5 torr at 135° C, and then filtered with diatomite to obtain 475 g of colorless ester containing no measurable hydrochloric or phosphoric acidity.

Ten grams of this ester is dissolved in 100 ml of trichloroethylene and left in open air in a 250 ml beaker with the addition of more trichloroethylene from time to time to maintain a constant level in the beaker. The solution remains completely neutral and limpid during three weeks. A sample of the dibromopropyl phosphate neutralized by ethylene oxide and acetic anhydride according to French Pat. No. 1,198,196, first addition, is subjected to the same test. In this case, the formation of glairy deposits and acidity is observed after a one-week exposure to open air.

EXAMPLE III

The process of Example II is repeated with the quantity of ethyl orthoformate reduced to 11 g. The final product contains about 92 meq/kg of phosphoric and hydrochloric acidity.

EXAMPLE IV

A process is carried out as in Example II with 20 g of ethyl orthoformate. The final product still contains only 17.5 meq/kg of phosphoric acidity.

EXAMPLE V

The process of Example II is repeated with a crude dibromopropyl phosphate containing 5.1 meq/kg of free HCl, 1.9 meg/kg of P—Cl and 230 meq/kg of P—OH. After heating for one hour at 115° C followed by one hour at 140° C with 4 percent of ethyl orthoformate, the product obtained did not have more than 53 meq/kg of phosphoric acidity, and it had no hydrochloric acidity.

EXAMPLE VI

This Example utilizes crude dibromopropyl phosphate prepared according to Example I and assaying 12.2 meq/kg of free HCl; 5.7 meq/kg of P—Cl; 170 meq/kg of P—OH; and no P—O—P. Five hundred grams of this phosphate is boiled with 100 g of methanol for 1 hour and then for an extra one-half hour after adding 100 ml of water and 5 ml of concentrated hydrochloric acid having a density of 1.18 g/cc.

After separation of the hydromethanolic layer, the phosphoric ester is dried under vacuum at 115° C and then heated for 1 hour at 115° C under nitrogen with 20 g of ethyl orthoformate and finally stripped under a pressure of 0.4 torr at 115° C. There is thus obtained a phosphoric ester without magnesium containing not more than 11 meq/kg of P—OH acidity and no hydrochloric acidity.

EXAMPLE VII

A sample of dibromopropyl phosphate is prepared according to the process described in Example I with a total acidity of 310 meq/kg, and 500 g of this phosphate is heated under nitrogen for two hours at 115° C with 35 g of commercial methyl orthoformate. After stripping at 115° C under 0.8 torr, the final product does not contain more than 24 meq/kg of total acidity.

EXAMPLE VIII

The process of Example VII is repeated using 41 g of commercial ethyl orthoacetate and heating for 1 hour at 115° C. After stripping at 115° C under 0.45 torr, the final product does not contain any detectable acidity.

EXAMPLE IX

Methyl orthocarbonate is prepared by adding dropwise one mole of trichloromethane sulfenyl chloride, $Cl_3C$—SCl, to a cooled methanolic solution containing 5 moles of sodium methylate. After 2 hours of repose at ambient temperature, the sodium chloride and the sulfur are separated by filtration, and the resulting filtrate is distilled under reduced pressure. This first distillate so obtained is then subjected to an extractive distillation in the presence of o-dichlorobenzene through a Vigreux column. The fraction passed between 35° and 60° C at 21 torr contains the main portion of the orthocarbonate and is saved. The orthocarbonate is then isolated from this fraction by recrystallization from ethyl ether at −60° C for a yield of 48%.

A 500 g sample of crude dibromopropyl phosphate identical to that used in Example VII is heated under nitrogen for 1 hour at 115° C with 47 g of the orthocarbonate prepared as above. After stripping under 1.2 torr at 115° C, the final product does not contain more than 5 meq/kg of total acidity.

EXAMPLE X

Methyl orthobenzoate is prepared by reacting one mole of trichloromethylbenzene with 3.15 moles of sodium methylate in methanolic solution for 20 hours at reflux. After filtration and rectification almost pure methyl orthobenzoate is obtained in a yield of 51%. The orthobenzoate has a boiling point at 15–16 torr of 102°–103° C, and $n_D^{25}$ of 1.4858, and contains 0.8% Cl.

Five hundred grams of crude dibromopropyl phosphate identical to that used in Example VII is heated under nitrogen for 1 hour at 115° C with 46 of the orthobenzoate. After stripping under 0.25 torr at 115° C, the final product does not contain detectable acidity.

EXAMPLE XI

Dibromopropyl orthoformate is prepared by the transesterification of one mole of ethyl orthoformate with six moles of dibromopropanol in the presence of one milliliter of methanesulfonic acid. After two hours and thirty minutes of heating at 120° C to 160° C with elimination of 132 g of light distillate rich in ethanol, the excess dibromopropanol is distilled off under 0.5 torr by raising the head temperature up to 140° C. The viscous residue weighs 436 g, has an $n_D^{25}$ of 1.577, and is essentially tris(dibromopropyl orthoformate, as confirmed by proton nuclear magnetic resonance (NMR).

Five hundred grams of the crude dibromopropyl phosphate identical to that used in Example VI is heated under nitrogen for 3 hours at 115° C wih 102 g of the tris(dibromopropyl) orthoformate so produced, and then is held at 140° C for 3 hours. The final product does not contain more than 75 meq/kg of total acidity.

What is claimed is:

1. A process for neutralizing tris(2,3-dibromo-1-propyl) phosphate containing phosphoric acid acid esters of dibromopropanol alone or with hydrohalic acidity, which comprises heating the phosphate with at least one carbon-containing orthoester having the formula $$Z—C(OY)_3$$

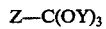

where Z is a hydrogen atom, a methyl or phenyl radical or an OY group and Y is a saturated aliphatic radical containing up to five carbon atoms or a 2,3-dibromo-1-propyl group.

2. A process according to claim 1 wherein the quantity of orthoester used is from 1.1 to 3 times stoichiometric.

3. A process according to claim 1 wherein the temperature is from 70° to 150° C.

4. A process according to claim 1 wherein the orthoester is trimethyl or triethyl orthoformate.

5. A process according to claim 1 wherein the orthoester is trimethyl or triethyl orthoacetate.

6. A process according to claim 1 wherein the orthoester is methyl orthocarbonate or orthobenzoate or 2,3-dibromo-1-propyl orthoformate.

7. A process according to claim 1 where the total acidity to be neutralized is not more than 500 meq/kg.

8. A process according to claim 1 wherein after heating with the orthoester, the resulting product is stripped under vacuum to provide the finished dibromopropyl phosphate.

9. A dibromopropyl phosphate prepared according to claim 1, the phosphate containing a quantity of the mixed phosphoric acid esters of 2,3-dibromo-1-propanol or of an alcohol having from formula YOH resulting from neutralization of said tris (2,3-dibromo-1-propyl) phosphate containing the acid esters and acidity.

* * * * *

UNITED STATES PATENT AND TRADEMARK OFFICE
CERTIFICATE OF CORRECTION

PATENT NO. : 4,059,656
DATED : November 22, 1977
INVENTOR(S) : MICHEL DEMARCQ

It is certified that error appears in the above-identified patent and that said Letters Patent are hereby corrected as shown below:

Front page, under data element identifier "[30]", change foreign application number from "75.2982" to --75.12982--.

Column 3, line 36, correct the spelling of "about"; line 36, correct the spelling of "stoichiometric"; line 56, change "as" to --an--.

Column 6, line 65, change "from" to --the--.

Signed and Sealed this

Fourteenth Day of March 1978

[SEAL]

Attest:

RUTH C. MASON
*Attesting Officer*

LUTRELLE F. PARKER
*Acting Commissioner of Patents and Trademarks*